US00PP36027P3

(12) United States Plant Patent
Jones et al.

(10) Patent No.: US PP36,027 P3
(45) Date of Patent: Jul. 23, 2024

(54) RASPBERRY PLANT NAMED 'N1237057'

(50) Latin Name: *Rubus idaeus*
Varietal Denomination: N1237057

(71) Applicant: Pacific Berries LLC, Ferndale, WA (US)

(72) Inventors: Lisa Jones, Lynden, WA (US); Julie Enfield, Lynden, WA (US); Joseph Stephens, Auckland (NZ)

(73) Assignee: Pacific Berries LLC

( * ) Notice: Subject to any disclaimer, the term of this patent is extended or adjusted under 35 U.S.C. 154(b) by 0 days.

(21) Appl. No.: 18/445,513

(22) Filed: Sep. 15, 2023

(65) Prior Publication Data

US 2024/0099169 P1 Mar. 21, 2024

Related U.S. Application Data

(60) Provisional application No. 63/408,752, filed on Sep. 21, 2022.

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./156, 203, 204
See application file for complete search history.

*Primary Examiner* — Karen M Redden
(74) *Attorney, Agent, or Firm* — Leydig, Voit & Mayer, Ltd.

(57) ABSTRACT

A new and distinct raspberry variety named 'N1237057' is described herein. The variety resulted from selection among a population of seedlings derived from a controlled cross carried out in 2012 between NN09030 (seed parent) (not patented) and NN08021 (pollen parent) (not patented). The present variety was selected for its yield, fruit firmness, vigour and harvest season.

4 Drawing Sheets

Genus and species plant named: *Rubus idaeus.*
Variety denomination: 'N1237057'.

BACKGROUND OF THE INVENTION

The variety resulted from selection among a population of seedlings derived from a controlled cross carried out in 2012 between 'NN09030' (seed parent) (not patented) and 'NN08021' (pollen parent) (not patented) located at Lynden, Washington, USA. 'N1237057' was identified in 2014 as having potential as a new variety due to its yield, fruit firmness, vigour and harvest season. 'N1237057' was first asexually propagated in 2017 through tissue culture in Ferndale, Washington USA. The resulting plants were planted in clonal trials and under went further evaluation. The plants were subsequently also found to be true to type demonstrating that the characteristics of the new variety are stable and transmitted without change through succeeding propagations.

SUMMARY OF THE INVENTION

'N1237057' is characterised by its dark red, short to medium sized fruit suitable for machine harvesting and processing; and excellent flavour.

Asexual reproduction of this new variety by cuttings and in vitro reproduction through tissue culture shows that the aforementioned characteristics are true to form and are established and transmitted through succeeding propagation.

COMPARISON WITH PARENTAL AND COMMERCIAL VARIETIES

TABLE 1

Comparison table between female parent NN09030 and candidate variety 'N1237057'

| Characteristic | NN09030 | 'N1237057' |
|---|---|---|
| Presence of spines | Absent | Present |
| Fruit firmness | Very firm | Soft to medium |

TABLE 2

Comparison table between male parent NN08021 and candidate variety 'N1237057'

| Characteristic | NN08021 | 'N1237057' |
|---|---|---|
| Fruit size | Small (2.3 grams) | Medium (3 grams) |
| Fruit colour | Medium red (44A) | Dark red (53A) |

TABLE 3

Comparison table between commercial variety 'Meeker' (not patented) and variety 'N1237057'

| Characteristic | 'Meeker' | 'N1237057' |
|---|---|---|
| Fruit firmness | Soft | Soft to medium |
| Fruit color | Red purple (59B) | Dark red (53A) |

TABLE 4

Comparison table between commercial variety 'Wakefield' (US Plant Patent No. 21185P3) and variety 'N1237057'

| Characteristic | 'Wakefield' | 'N1237057' |
|---|---|---|
| Time of beginning of fruiting | Late | Early to medium |

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

Figure 1:
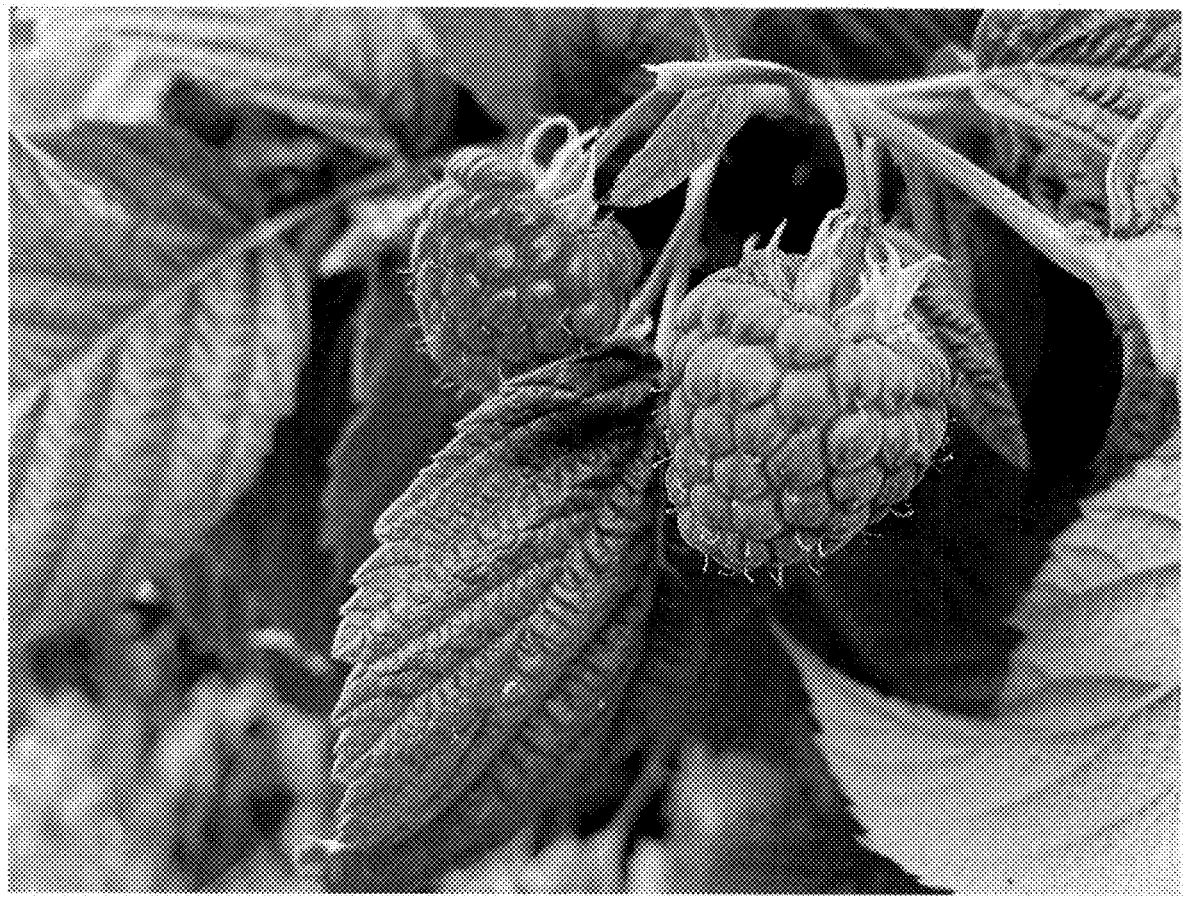

FIG. 1: Fruit of 'N1237057' in the field.

Figure 2:
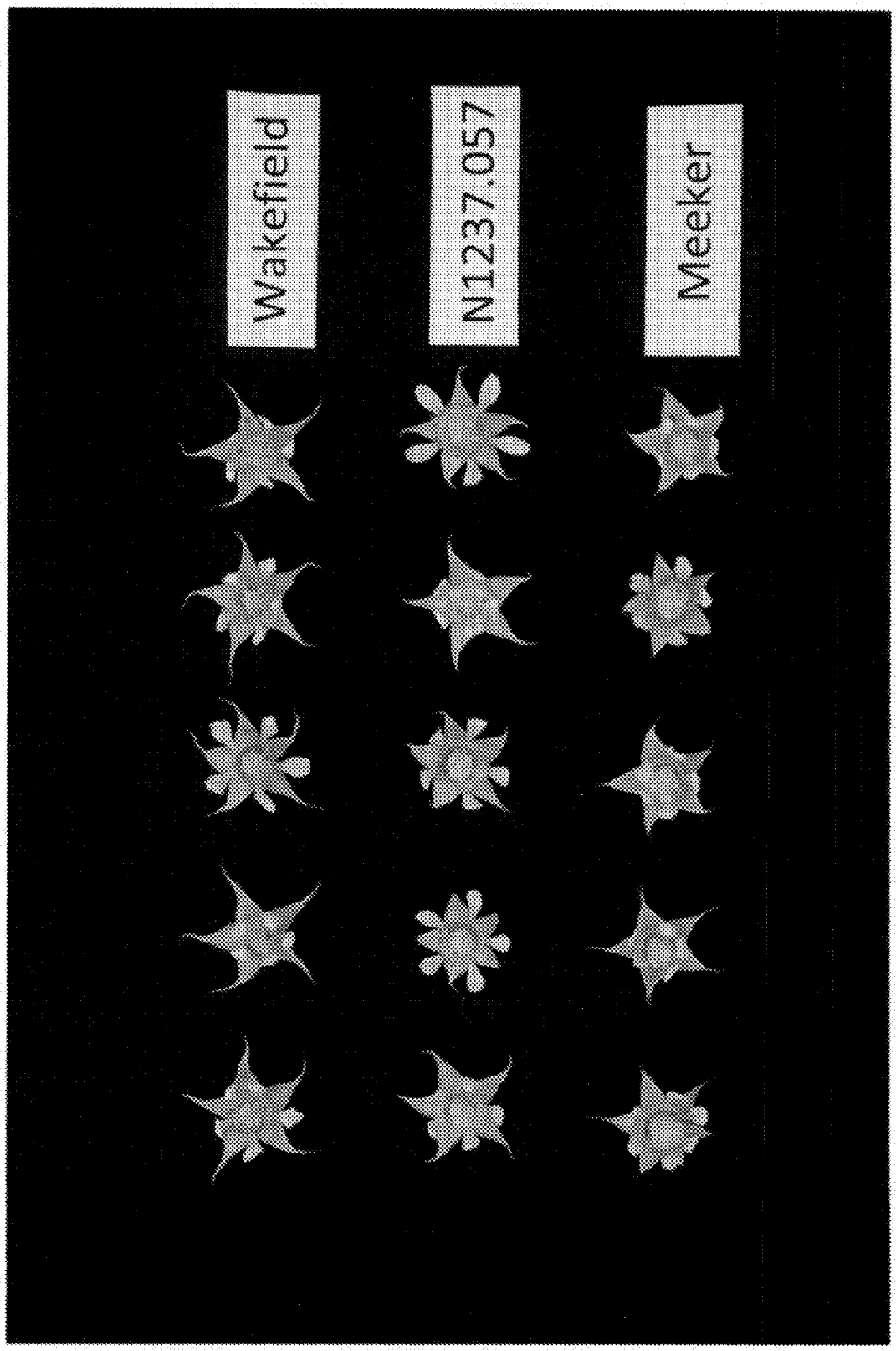

FIG. 2: Flowers of 'N1237057' (middle) compared to 'Wakefield' (top) and 'Meeker' (bottom).

Figure 3:
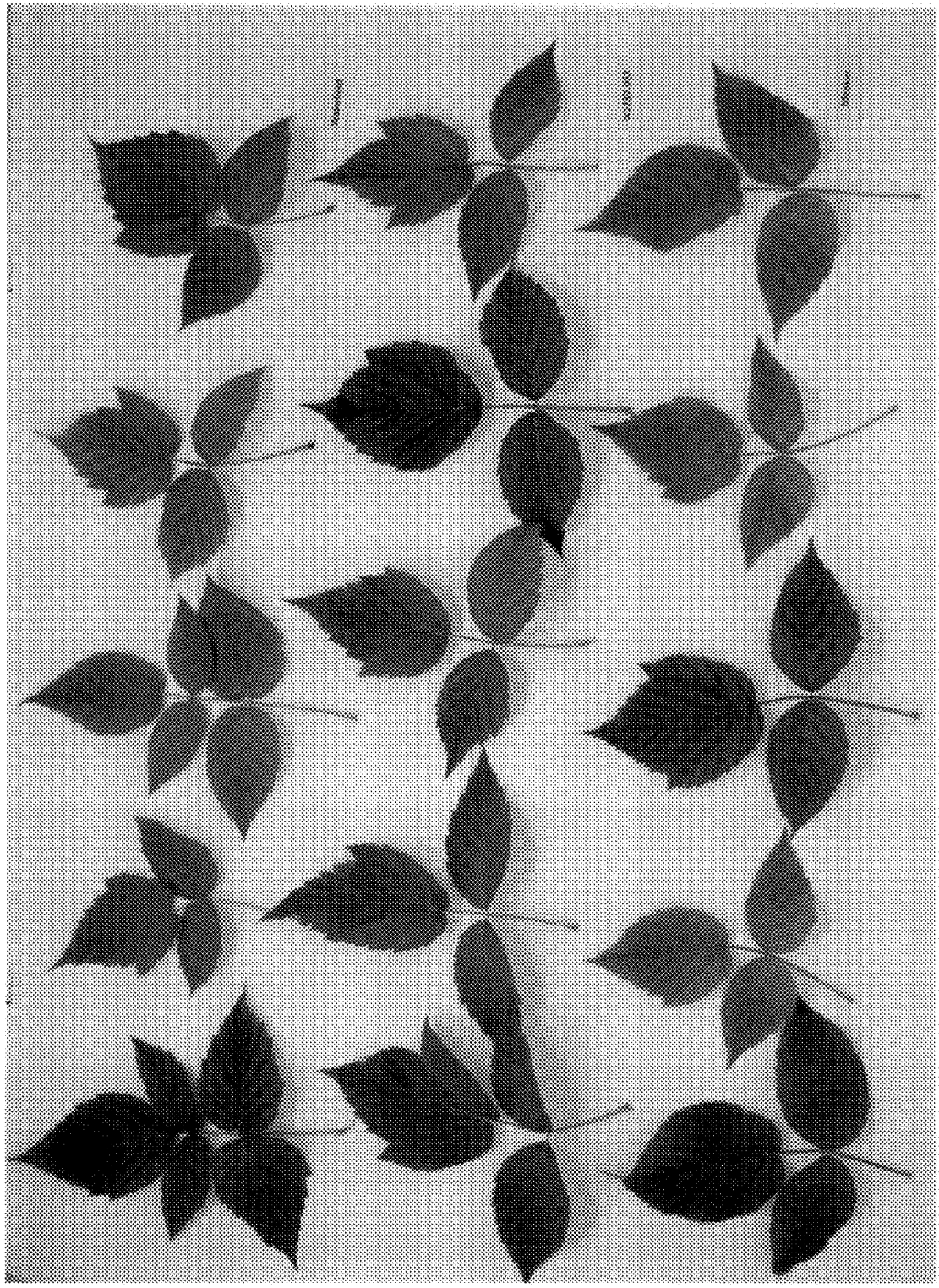

FIG. 3: Leaves of 'N1237057' (middle) compared to 'Wakefield' (top) and 'Meeker' (bottom).

Figure 4:
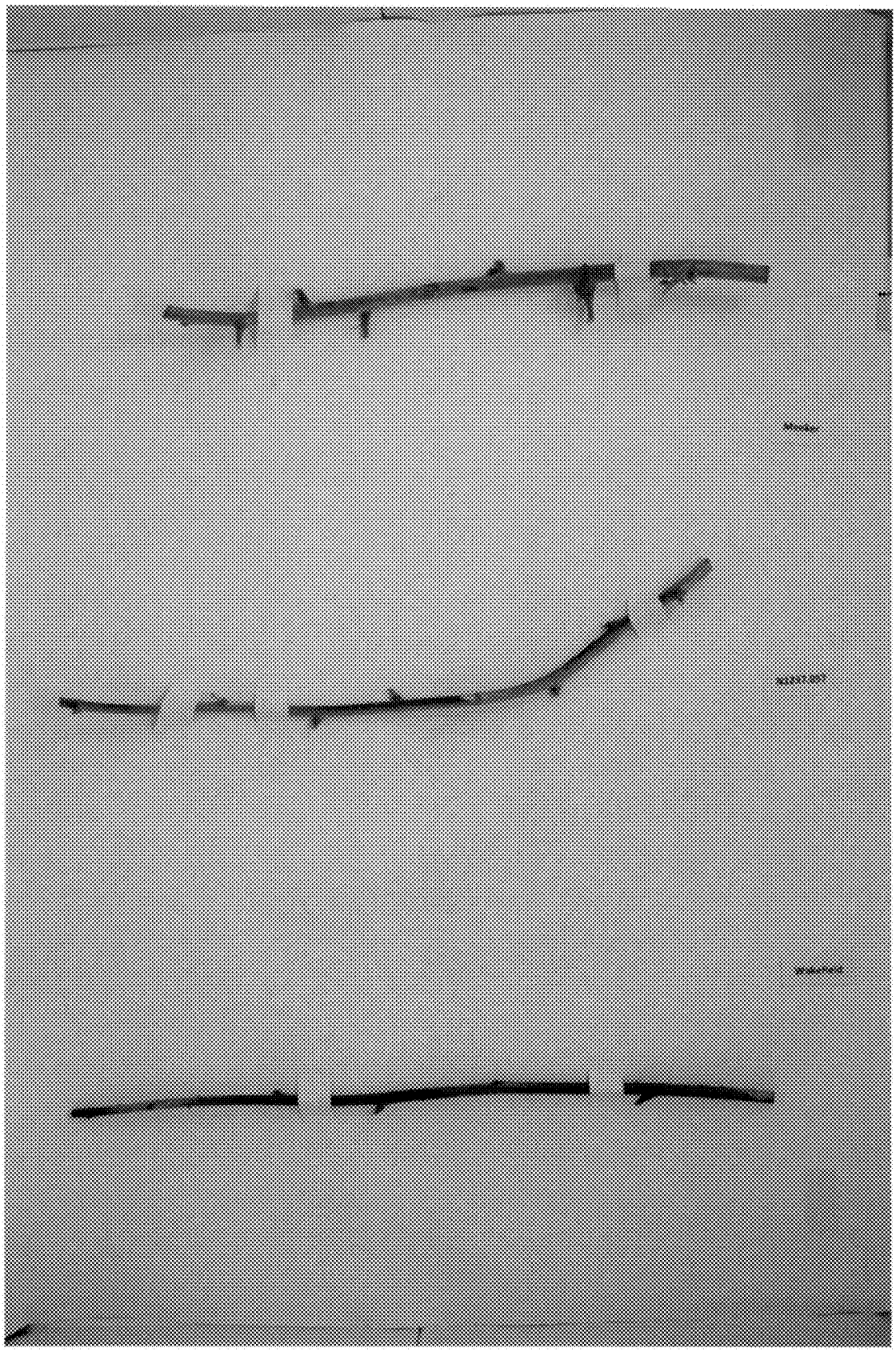

FIG. 4: Stems of 'N1237057' (middle) compared to 'Wakefield' (bottom) and 'Meeker' (top).

DETAILED BOTANICAL DESCRIPTION

The following is a description of the new variety with color terminology in accordance with The Royal Horticultural Society Colour Charts (R.H.S.C.C.) 5th edition.

The specimens described were grown in Washington, USA. The observations were made in the 2020-2022 season on 2-4 year old plants.

Plant:
- *Habit*.—Upright.
- *Number of current seasons canes*.—Medium, average 12.
- *Overall plant height*.—Average 232 cm.
- *Overall plant width*.—Average 63 cm.

Very young shoot:
- *Anthocyanin colouration of apex during rapid growth*.—Present, near dark purple red 59A.
- *Intensity of anthocyanin colouration of apex during rapid growth*.—Strong.
- *Attitude*.—Erect.

Current seasons canes:
- *Bloom*.—Absent or very weak.
- *Anthocyanin colouration*.—Weak to medium; near medium purple red, 59D.
- *Length of internode*.—Short to medium; average, 76 mm.
- *Number of internodes per cane*.—Average, 37.
- *Length of vegetative bud*.—Medium; average, 10 mm.

Varieties that fruit on previous season's canes in summer:
- *Dormant cane length*.—Medium; average, 221 cm.
- *Dormant cane width*.—Average, 10 mm.
- *Dormant cane color*.—Brown, 164A.
- *Dormant cane pubescence*.—Absent.

Mature canes:
- *Coloration on sunny side*.—Near dark brown purple, 178A.
- *Coloration on shady side*.—Near light green, 145A.

Spines:
- *Density*.—Very sparse to sparse; average less than 30 cm from base, 18 $cm^2$; average more than 1 m from base, 1.
- *Size of base*.—Very small; average, 3 mm.
- *Length*.—Very short; average 1 mm.
- *Color*.—Purple; near dark brown N77A and near light green 145B.

Leaves:
- *Green color of upper side*.—Medium to dark; near medium brown green 137C.
- *Colour of lower side of leaf*.—near dark brown green N138C.
- *Predominant number of leaflets*.—Three.
- *Profile of leaflets in cross section*.—Concave.
- *Rugosity*.—Strong.
- *Relative position of lateral leaflets*.—Free.
- *Terminal leaflet length*.—Short to medium; average, 115 mm.
- *Terminal leaflet width*.—Medium; average 73 mm.
- *Terminal leaflet tip shape*.—Acuminate.
- *Lateral leaflet length*.—Short; 96 mm.
- *Lateral leaflet width*.—Narrow to medium; average, 49 mm.
- *Leaf shape*.—Compound.
- *Leaf pubescence on upper side*.—Matte.
- *Total leaf length*.—Average, 199 mm.
- *Total leaf width*.—Average, 225 mm.
- *Leaf margin*.—Serrate.
- *Venation pattern*.—Pinnate.
- *Venation color*.—Near light green, N144D.

Petiole:
- *Length*.—Average, 44 mm.
- *Width*.—Average, 3 mm.
- *Hairs*.—Present.
- *Color*.—Near light green, N144D.
- *Anthocyanin colouration on upper side of petiole*.—Near orange red, N34D.
- *Spines*.—Present.

Flower pedicel:
- *Number of spines*.—Absent to very few; average, 2 per $cm^2$.
- *Length*.—Average, 18 mm.
- *Width*.—Average, 1 mm.
- *Color on the sunny side*.—Near brown red, 182B.
- *Color on the shady side*.—Near medium green, 144A.
- *Hairs/spines*.—Present.
- *Length of hairs/spines*.—Average, <1 mm.

Flower peduncle:
- *Presence of anthocyanin colouration*.—Absent.
- *Length*.—16 mm.
- *Width*.—1 mm.
- *Hairs/spines*.—Present.

Flower:
- *Size*.—Small to medium; average diameter of the whole flower, 27 mm.
- *Petal length*.—Average, 8 mm.
- *Petal width*.—Average, 3 mm.
- *Number of petals per flower*.—Average, 5.
- *Petal shape*.—Obovate.
- *Petal tip shape*.—Rounded.
- *Petal base shape*.—Wedge shaped concave.
- *Petal texture*.—Smooth.
- *Petal venation pattern*.—Longitudinal.
- *Petal margin*.—Entire.
- *Petal color*.—Near white, NN155D.
- *Number of sepals per flower*.—Average, 5.
- *Sepal color*.—Near light green, 139D.
- *Sepal size*.—Average, 11 mm.
- *Number of stamens per flower*.—Average, 71.

*Stamen color*.—Near white, NN155D.
*Filament length*.—Average, 5 mm.
*Filament color*.—Near white, NN155C.
*Anther length*.—Average, 1 mm.
*Anther color*.—Near light yellow orange, 158A.
*Number of stigmas per flower*.—Average, 78.
*Stigma color*.—Near light green, 157A.
*Fragrance*.—Absent.

Varieties which fruit on previous year's canes in summer:
*Fruiting lateral attitude*.—Semi-erect.
*Fruiting lateral length*.—Short to medium; average, 69 mm.
*Fruiting lateral colour*.—Near light green, N144D.
*Fruiting lateral width*.—Average, 5 mm.
*Number of fruit per lateral*.—Average, 12.

Fruit:
*Length*.—Short to medium; average, 19 mm.
*Weight*.—Average, 3 g.
*Width*.—Narrow to medium; average, 19 mm.
*Ration length/width*.—Small.
*Cavity diameter*.—Average, 9 mm.
*Cavity depth*.—Average, 12 mm.
*Receptacle length*.—Average, 14 mm.
*Receptacle width*.—Average, 7 mm.
*Receptacle shape*.—Rounded and pointed.
*General shape in lateral view*.—Circular.
*Size of single drupe*.—Small; average, 4 mm; average per fruit, 78.
*External color*.—Dark red, 53A.
*Internal color*—Dark red, 53A.
*Glossiness*.—Weak.
*Firmness*.—Soft to medium, average 55 g/mm.
*Adherence to plug*.—Weak.
*Main bearing type*.—Only on previous year's cane in summer.
*Hairs*.—Present.
*Number of seeds per fruit*.—Average, 78.
*Seed weight*.—Average 1.8 mg.
*Seed color when dry*.—Near light orange, 26C.
*Seed length*.—Average, 3 mm.
*Seed width*.—Average, 2 mm.
*Flavour*.—Tart and strong.
*Yield per plant*.—Average, 4.5kg.

Varieties which fruit on previous year's canes in summer timing:
*Time of vegetative bud burst*.—Early to medium; average, 20$^{th}$ of March.
*Time of beginning of flowering on previous year's cane*.—Early to medium; average, 20$^{th}$ of May.
*Time of beginning of fruit ripening on previous year's cane*.—Early to medium; average, 15$^{th}$ of June.
*Length of fruiting period on previous year's cane*.—Short to medium; average 20$^{th}$ of June to 31$^{st}$ of July.

We claim:

1. A new and distinct raspberry plant named 'N1237057' substantially as illustrated and described herein.

* * * * *